US00PP13319P2

(12) United States Plant Patent
Zary

(10) Patent No.: US PP13,319 P2
(45) Date of Patent: Dec. 3, 2002

(54) SHRUB ROSE PLANT NAMED 'JACIGNAT'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 25 days.

(21) Appl. No.: 09/695,778

(22) Filed: Oct. 24, 2000

(51) Int. Cl.[7] ..... A01H 5/00
(52) U.S. Cl. ..... Plt./107
(58) Field of Search ..... Plt./107

(56) References Cited

U.S. PATENT DOCUMENTS

PP7,220 P * 4/1990 Austin ..... Plt./107

* cited by examiner

*Primary Examiner*—Bruce R. Campell
*Assistant Examiner*—W C Baker
(74) *Attorney, Agent, or Firm*—Klarquist Sparkman, LLP

(57) ABSTRACT

Shrub rose plant having a vigorous, upright growth habit; large clusters of medium-sized flowers; a strong clove scent that degrades to a strong musk; dark green, healthy foliage; profusion of small prickles on flowering wood; and an ability to own root easily.

1 Drawing Sheet

The present invention relates to a new and distinct variety of rose plant of the shrub class which was originated by me by crossing the variety LaMarne (not patented) with the variety MACman (not patented).

The primary objective of this breeding was to produce a new rose variety having the shrub habit and plant disease resistance of the female parent combined with the larger flowers of the male parent. The objective was substantially achieved, along with other desirable improvements, as evidenced by the following unique combination of characteristics that are outstanding in the new variety and that distinguish it from its parents, as well as from all other varieties of which I am aware:

1. Vigorous, upright, rounded growth habit;
2. Large clusters of medium sized flowers;
3. Strong clove scent;
4. Dark green, healthy foliage;
5. Profusion of small prickles on flowering wood; and
6. Ability to own root easily.

Asexual reproduction of this new variety by cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:
*Seed parent.*—LaMarne (not patented).
*Pollen parent.*—MACman (not patented).
Classification:
*Botanical.*—*Rosa hybrida.*
*Commercial.*—Shrub.

FLOWER

Observations made from specimens grown in a garden environment at Somis, Calif., at 3 years of age in January, 1999 to July, 2000.

Blooming habit: Continuous.
Bud:
*Size.*—Three-quarters of an inch long when the petals start to unfurl.
*Form.*—The bud form is short, pointed ovoid.
*Color.*—When sepals first divide, bud color is Purple Group 75A. When half blown, the upper sides of the petals are Purple Group 75C; and the lower sides of the petals are Purple Group 75D on the outer third of the petal, then Red-Purple Group 66D on the inner two-thirds.
*Sepals.*—Color: Green Group 138B. Surface texture: Covered in fine hairs. There are three lightly appendaged sepals. There are two unappendaged sepals with hairy edges.
*Receptacle.*—Color: Yellow-Green Group 146B with Greyed-Purple Group 183C if exposed to bright sunlight. Shape: Funnel. Size: Medium, about 7/16"× ¼" Surface: Smooth.
*Peduncle.*—Length: Medium, averaging about 3 inches. Surface: Very glandular. Color: Yellow-Green Group 146C except when exposed to bright sunlight, then Greyed-Red Group 178A. Strength: Bending and slender.
Bloom:
*Size.*—Medium. Average open size is 3½ inches.
*Borne.*—Several together in pyramidal, rounded, irregular shaped clusters of 5 to 15 blooms.
*Stems.*—Strength: Strong. Average length is about 14 inches to 16 inches.
*Form.*—When first open: Bloom is rounded/spherical. Permanence: Flattens and outer petals curl back.
*Petalage.*—Number of petals under normal conditions: 60–70.
*Color.*—The upper sides of the petals are Red-Purple Group 57C. The reverse sides of the petals are Red-Purple Group 57C on the outer third of the petals, then Red-Purple Group 66D on the inner third. The base of each petal has on the upper surface a distinct Yellow Group 3C ¼"×¼" color spot. On the lower side there is a ⅜"×⅜" Yellow Group 2D color spot. The major color on the upper side is Red-Purple Group 57C.

*Variegations.*—There are occasional whitish yellow streaks (Yellow Group 2D) on the petals.

*Discoloration.*—The general tonality at the end of the first day: No change. At the end of the third day: A lightening of the flower color to Red-Purple Group 57D. At the end of the fifth day: The color has faded to Red-Purple Group 66D. At the end of the sixth day: Petals drop.

*Fragrance.*—Strong. Character of Fragrance: Clove, on newly opened bloom. Changes by day five to a strong musk scent, a degradation of fragrance.

Petals:

*Texture.*—Thin.

*Shape.*—Round to deltoid except for the inner petals which are oblanceolate.

*Form.*—Tips slightly curved.

*Arrangement.*—Imbricated, except for the inner most petals which are irregular. Petaloids in the center are few (0–7) and small (¼"×⅛"), and Red-Purple Group 57C in color.

*Persistence.*—Petals drop off cleanly before drying.

*Lastingness.*—On the plant: Fair (about five days). As a cut flower: Fair (about six days).

Reproductive parts:

*Stamens.*—Number: 70–90. Anthers: Size: Medium. Color: Yellow-Orange Group 16C. Arrangement: Regular around styles. Filaments: Color: Yellow Group 2C. Pollen: Color: Yellow-Orange Group 22C.

*Pistils.*—Number: 60–80. Styles: Color: Greyed-Purple Group 183B. Stigmas: Color: Orange-White Group 159C. Hips: None observed.

Plant:

*Form.*—Shrub.

*Growth.*—Vigorous, upright, branching. At maturity, height is 4 feet, width is 3 feet. Blooms three months after planting.

Foliage: Number of leaflets on normal mid-stem leaves: 7 or 9.

*Size.*—Large (6½" long×4 ½" wide).

*Quantity.*—Abundant.

*Color.*—New foliage: Upper surface: Green Group 136A. Lower surface: Yellow-Green Group 146B. Old foliage: Upper surface: Greyed-Red Group 178A. Lower surface: Greyed-Red Group 178A.

Leaflets:

*Length.*—2–2½ inches.

*Width.*—1¼–1½ inches.

*Shape.*—Ovate. Apex Shape: Cuspidate. Base Shape: Rounded.

*Texture.*—Upper surface: Coriaceous, nitid. Lower surface: Hoary.

*Edge.*—Serrated.

*Serration.*—Single, small.

*Petiole rachis.*—Color: Green Group 137A on both surfaces.

*Petiole underside.*—Rough with prickles.

*Stipules.*—Medium, serrated (about ⅝ inch), bearded.

*Disease resistance.*—Resistant to mildew and rust, susceptible to blackspot under normal growing conditions.

Wood:

*New wood.*—Color: Yellow-Green Group 146B except on the newest wood which is Greyed-Red Group 178B. Bark: Smooth.

*Old wood.*—Color: Green Group 137A. Bark: Smooth.

Prickles:

*Quantity.*—On main canes from base and on laterals: 18–22 per six inches of stem.

*Form.*—Medium, straight.

*Color when young.*—Greyed-Red Group 178B.

*Color when mature.*—Greyed-Red Group 178D.

Small prickles:

*Quantity.*—On main stalks and laterals: 50–60 per six inches of stem. There are no small prickles on the lower main wood, but are on the upper flowering wood only.

*Color.*—Greyed-Red Group 178B.

I claim:

1. A new and distinct variety of rose plant of the shrub class, substantially as herein shown and described, characterized particularly by its vigorous, upright growth habit; large clusters of medium-sized flowers; a strong clove scent that degrades to a strong musk; dark green, healthy foliage; profusion of small prickles on flowering wood; and an ability to own root easily.

* * * * *

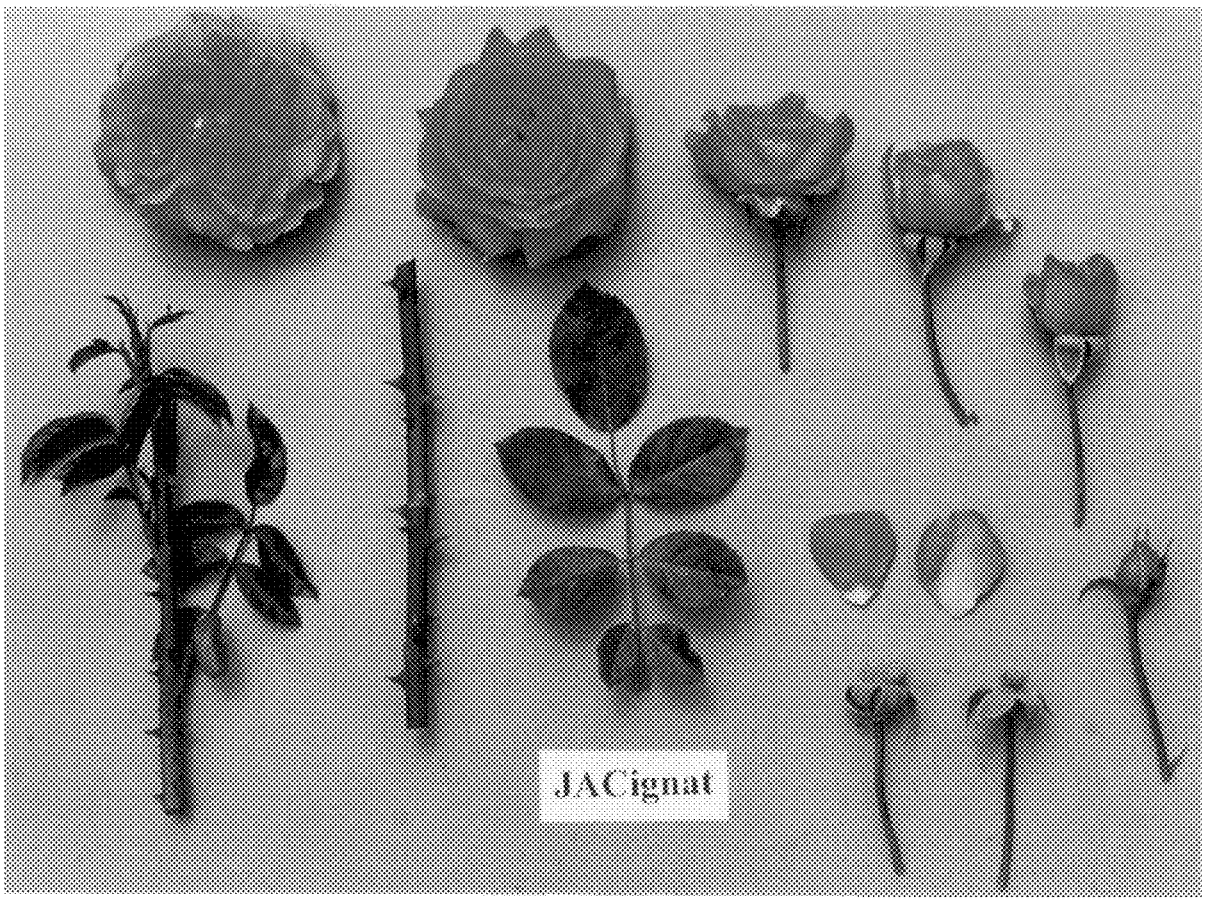
JACignat